(12) United States Patent
Koehler et al.

(10) Patent No.: US 9,490,873 B2
(45) Date of Patent: Nov. 8, 2016

(54) METHODS AND APPARATUS FOR UNDERWATER ELECTRICAL NEAR-FIELD SIGNAL SYSTEM

(71) Applicant: Raytheon Company, Waltham, MA (US)

(72) Inventors: Frederick B. Koehler, Tucson, AZ (US); Thomas P. Mccreery, Tucson, AZ (US); Robert Rinker, Tucson, AZ (US); Darrell R. Rogers, Tucson, AZ (US); Ross D. Rosenwald, Tucson, AZ (US); Terry M. Sanderson, Tucson, AZ (US); David R. Sar, Corona, CA (US); Ernest D. Fasse, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 95 days.

(21) Appl. No.: 14/504,689

(22) Filed: Oct. 2, 2014

(65) Prior Publication Data
US 2016/0099751 A1    Apr. 7, 2016

(51) Int. Cl.
| | |
|---|---|
| *H04B 13/02* | (2006.01) |
| *H04B 5/00* | (2006.01) |
| *G01N 25/00* | (2006.01) |
| *G01N 27/06* | (2006.01) |
| *G06F 1/16* | (2006.01) |
| *H04W 4/00* | (2009.01) |

(Continued)

(52) U.S. Cl.
CPC ............ *H04B 5/0031* (2013.01); *G01N 25/00* (2013.01); *G01N 27/06* (2013.01); *G01S 1/72* (2013.01); *G06F 1/163* (2013.01); *G06F 1/1698* (2013.01); *H04B 13/02* (2013.01); *H04W 4/008* (2013.01); *H04B 2001/3894* (2013.01)

(58) Field of Classification Search
CPC .................. H04B 5/0043; H04B 5/00; H04B 2001/3894
USPC ................................ 455/40, 41.1, 41.2, 41.3
See application file for complete search history.

(56) References Cited

U.S. PATENT DOCUMENTS

| | | | | |
|---|---|---|---|---|
| 4,833,413 | A  * | 5/1989 | Head .................... | G01N 27/07 324/444 |
| 2006/0286931 | A1 | 12/2006 | Rhodes et al. | |
| 2007/0230268 | A1* | 10/2007 | Hoogeveen ............. | G01S 5/22 367/19 |
| 2009/0141591 | A1* | 6/2009 | Basilico ................... | G01S 1/72 367/128 |

(Continued)

FOREIGN PATENT DOCUMENTS

WO    WO 2006/134329 A2    12/2006

OTHER PUBLICATIONS

International Application No. PCT/US2015/040677, Notification of Transmittal of the International Search Report and the Written Opinion of the International Searching Authority, or the Declaration, date of mailing Jan. 15, 2016, 17 pages.

(Continued)

*Primary Examiner* — Tuan Pham
(74) *Attorney, Agent, or Firm* — Daly, Crowley, Mofford & Durkee, LLP (57) ABSTRACT

Methods and apparatus for a near-field signal system to generate signals underwater for navigation and/or communication. In one embodiment, a system includes a signal processing module coupled to a first antenna to transmit near-field signals underwater and a second antenna to receive near-field signals underwater transmitted by the first antenna. In one embodiment, a wetsuit includes an integrated near-field signal system.

22 Claims, 8 Drawing Sheets

(51) Int. Cl.
*G01S 1/72* (2006.01)
*H04B 1/38* (2015.01)

(56) References Cited

U.S. PATENT DOCUMENTS

| | | | | |
|---|---|---|---|---|
| 2014/0065953 A1* | 3/2014 | Rhodes | ............... | H04B 13/02 |
| | | | | 455/40 |
| 2014/0159901 A1* | 6/2014 | Copeland | ........... | G08B 13/2468 |
| | | | | 340/572.3 |
| 2014/0350836 A1* | 11/2014 | Stettner | ............... | G01S 17/023 |
| | | | | 701/301 |
| 2016/0069674 A1* | 3/2016 | Govoni | ............... | G01B 21/00 |
| | | | | 702/150 |

OTHER PUBLICATIONS

PCT Partial Search Report and Invitation to Pay Additional Fees dated Oct. 30, 2015; for PCT Pat. App. No. PCT/US2015/040677; 6 pages.

* cited by examiner

$$q = \pm \frac{1}{4} \frac{\in LV}{k_c}$$

METHODS AND APPARATUS FOR UNDERWATER ELECTRICAL NEAR-FIELD SIGNAL SYSTEM

BACKGROUND

As is known in the art, there are a variety of challenges in providing underwater navigation and communication capabilities. For example, underwater communication is limited by the signal propagation characteristics of water. While certain acoustic signals may propagate in water, it may be undesirable for other entities to detect the presence of these signals. Underwater communication may be provided by an acoustic transducer with a range of 6 km, for example, but such systems are not stealthy. While sonar systems may be useful in many applications, sonar may have a relatively narrow field of view and is not stealthy.

In addition, GPS signals for navigation are not readily detectable underwater. Further, divers in harsh environments, such as rescue and oil rigs, may dive at night with little or no visibility, which can be relatively hazardous. Even with illumination, it may be difficult to see potentially dangerous objects in murky water.

SUMMARY

The present invention provides methods and apparatus for near-field signal systems that can provide underwater navigation and/or communication by emitting a frequency modulated DC current that can transmit signals, determine bearing of a signal, and locate conductive and non-conductive objects. In embodiments, a near-field signal system is configured to form part of a diver wetsuit apparatus having a signal range in the order of tens or hundreds of meters. In another embodiment, an underwater vehicle includes a near-field signal system.

In one aspect of the invention, a near-field signal system to generate signals underwater, comprises: a signal processing module; a first antenna to transmit electrical near-field signals underwater coupled to the signal processing module; and a second antenna to receive near-field signals underwater transmitted by the first antenna.

The system can further include one or more of the following features: a salinity sensor to measure salinity of water coupled to the signal processing module, a temperature sensor to obtain temperature information for the water coupled to the control module, the second antenna includes a dipole array, a user interface to display information on objects detected by the second antenna, the user interface includes a head up display, the user interface includes a sound generator, the near-field signal system forms a part of a wetsuit, and/or the near-field signal system forms part of an underwater vehicle.

In another aspect of the invention, a method comprises: transmitting electrical near-field signals underwater by a first antenna; receiving near-field signals underwater transmitted by the first antenna; and processing the received near-field signals to provide information to a user.

The method can further include one or more of the following features: the information comprises navigation information to avoid objects, the information comprises communication data from another underwater entity, using water salinity to process the received near-field signals, using temperature information for the water coupled to process the received near-field signals, receiving the near-field signals with a second antenna that includes a dipole array, formatting the processed information for display to a user, the first antenna forms a part of a wetsuit, and/or the first antenna forms a part of an underwater vehicle.

In a further aspect of the invention, a system comprises: a display; and a signal processing means coupled to the display, the signal processing means to generate signals for transmission of electrical near-field signals underwater by a first antenna and to process near-field signals transmitted by the first antenna and received by a second antenna.

The system can further include one or more of the following features: a salinity sensor to measure salinity of water coupled to the signal processing module, a temperature sensor to obtain temperature information for the water coupled to the control module, the second antenna includes a dipole array, a user interface to display information on objects detected by the second antenna, the user interface includes a head up display, the user interface includes a sound generator, the near-field signal system forms a part of a wetsuit, and/or the near-field signal system forms part of an underwater vehicle.

In a further aspect of the invention, a near field communication system for generating signals underwater, comprises: a signal processing module; a first antenna to transmit; a second antenna to receive near field signals originating from a further near field communication system that is underwater, wherein the first antenna and the second antenna are connected to the signal processing module.

The system can further include one or more of the following features: a salinity sensor to measure salinity of water coupled to the signal processing module, a temperature sensor to obtain temperature information for the water coupled to the control module, the second antenna includes a dipole array, a user interface to display information on objects detected by the second antenna, the user interface includes a head up display, the user interface includes a sound generator, the near-field signal system forms a part of a wetsuit, and/or the near-field signal system forms part of an underwater vehicle.

In a further aspect of the invention, a near field signal system for generating signals underwater comprises: a signal processing module; a first antenna to transmit a navigation signal, a communication signal, or both; a second antenna to receive the navigation signal from the first antenna or a communication signal from a further near field signal system, wherein first and second antennas are connected to the signal processing module, and wherein the signal processing module is configured to interpret the received signals as either the navigation signal from the first antenna or the communication signal from the further near field signal system.

The system can further include one or more of the following features: a salinity sensor to measure salinity of water coupled to the signal processing module, a temperature sensor to obtain temperature information for the water coupled to the control module, the second antenna includes a dipole array, a user interface to display information on objects detected by the second antenna, the user interface includes a head up display, the user interface includes a sound generator, the near-field signal system forms a part of a wetsuit, and/or the near-field signal system forms part of an underwater vehicle.

BRIEF DESCRIPTION OF THE DRAWINGS

The foregoing features of this invention, as well as the invention itself, may be more fully understood from the following description of the drawings in which.

DETAILED DESCRIPTION

Figure 1:
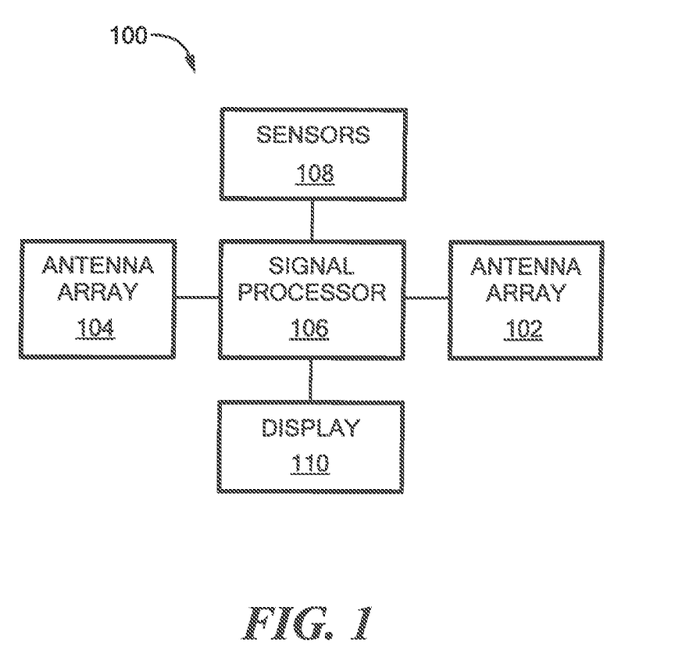
FIG. 1 is a schematic representation of underwater system near-field signal processing.

FIG. 1 shows an illustrative near-field signal system 100 to send and receive electrical signals underwater. A first antenna array 102 includes a dipole array, for example, to transmit signals into the surrounding water and a second antenna array 104 to receive signals. A signal processor 106 is coupled to the first and second antenna arrays 102, 104 to control signal transmission and receive operations. At least one sensor 108 can be coupled to the signal processor to provide water temperature, salinity, depth, etc., that can be used for processing signals, as described more fully below. A user interface 110 can provide various visual, audio, and/or vibratory information to a user, such as in a diving mask.

It is understood that the near-field signals do not propagate or echo so as to be detectable beyond a relatively short distance. As used herein, near-field electrical signals refers to signals that are a non-radiative time-varying electromagnetic field.

Embodiments of the invention utilize near field electrical signals and sensors to detect objects and/or communicate with other divers and/or UUVs (unmanned underwater vehicles). In one embodiment, a system is integrated into a wetsuit with transmit and receive arrays 102, 104. Information can be displayed for a user in a heads up manner and/or provided as audio via speakers and microphones. For example, first and second divers can communicate using near-field electrical signals in a manner that is not detectable beyond a certain distance using conventional equipment.

Figure 2:
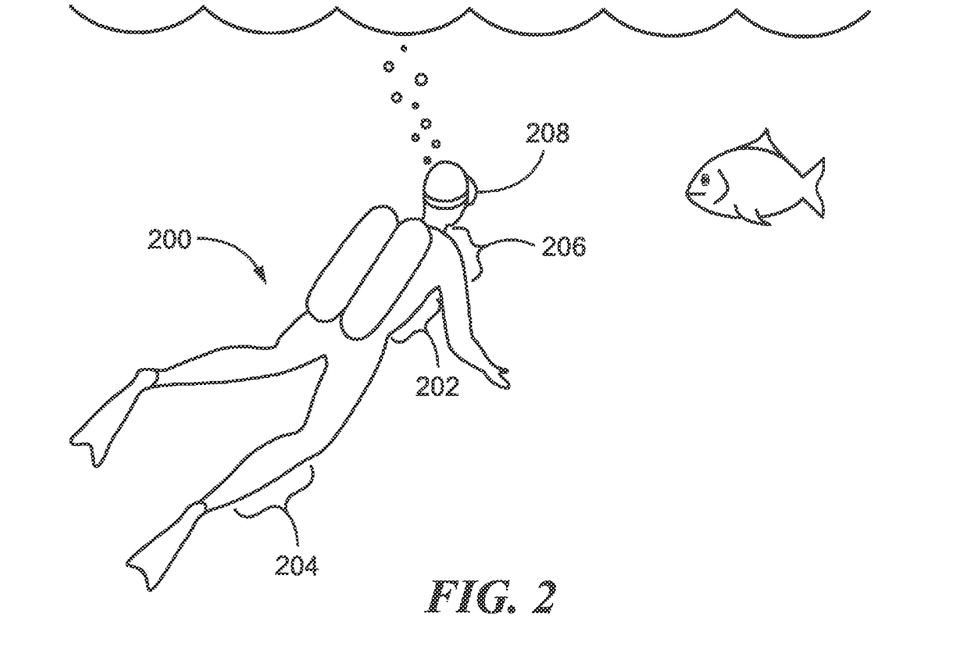
FIG. 2 is a schematic representation of a near-field signal system integrated with a wetsuit.

FIG. 2 shows a wetsuit 200 having a transmit array 204 and a receive array 202. A control module 206 controls signal transmit and receive functionality. A user interface 208 can be integrated with a divers mask. The wetsuit 200 allows freedom of motion underwater while providing communication and/or navigation capability.

It is understood that a wide variety of suitable antennas and materials can be used to meet the needs of a particular application. In one embodiment, antennas are provided as dipoles with finite end geometry having point sources, e.g., tinned wire ends, to four inch square copper plates, for example. In general, larger antenna plates provide enhanced performance for range and sensitivity than the point sources. It is understood that the separation distance of the dipoles can be selected to meet the needs of a particular application. In general, a larger dipole separation tends to provide better distance capability. In one particular embodiment, dipole separation ranges from about two inches to five inches. In another embodiment, conformal antennas can be used.

It is further understood that the number and placement of dipole arrays can be selected to meet the needs of a particular application. In one embodiment, dipole arrays are placed on a wetsuit so the arrays are located around a diver, vehicle or sensor. Antennas can be used to transmit and/or receive and can be cycled to determine bearing and range.

In one embodiment, the transmitted signals are frequency modulated DC currents, such as from about DC to about 10 MHz. In one embodiment, receivers are sensitive in the micro-volt range. The frequency modulated signal can be used to transmit voice signals via microphone and, once received, communicated through a speaker or earpiece. The signals may also be used to transmit information in the form of text, still pictures, or video that can be displayed on a monitor, such as a heads up display inside a diver mask, on a display worn on a diver forearm, or on any other suitable visual display or indicator.

It is understood that temperature and salinity of the water can have a significant impact on the propagation characteristics of the water. Temperature and salinity of the water are measured in real time to improve result accuracy.

Figure 3:
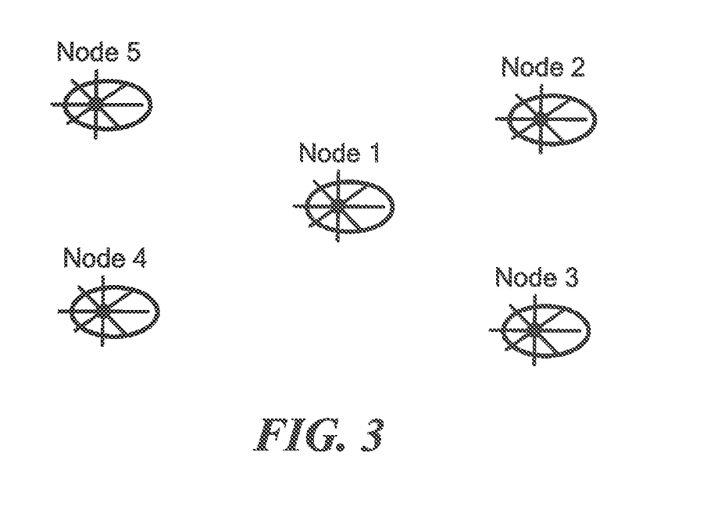
FIG. 3 is a schematic representation of a dipole array that can form part of a near-field communication system.

FIG. 3 shows a sensor array 300 with an array of dipoles 302. An array of three or more dipoles 302 allows triangulation of bearing and range of each node with respect to one another. In one embodiment, a receiver can be modeled as a dipole with anode/cathode charges as:

$$q = \pm \frac{1}{4} \frac{\epsilon LV}{k_C},$$

where: $\epsilon \approx 50$ is the relative permittivity of water, $L=5$ inches, is the anode-cathode separation distance, V is the semi-amplitude of the sinusoidal applied voltage (maximum difference between anode and cathode voltages), and $K_c=8.987552e+09$ $Nm^2/C^2$ is Coulomb's constant.

Figure 3A:
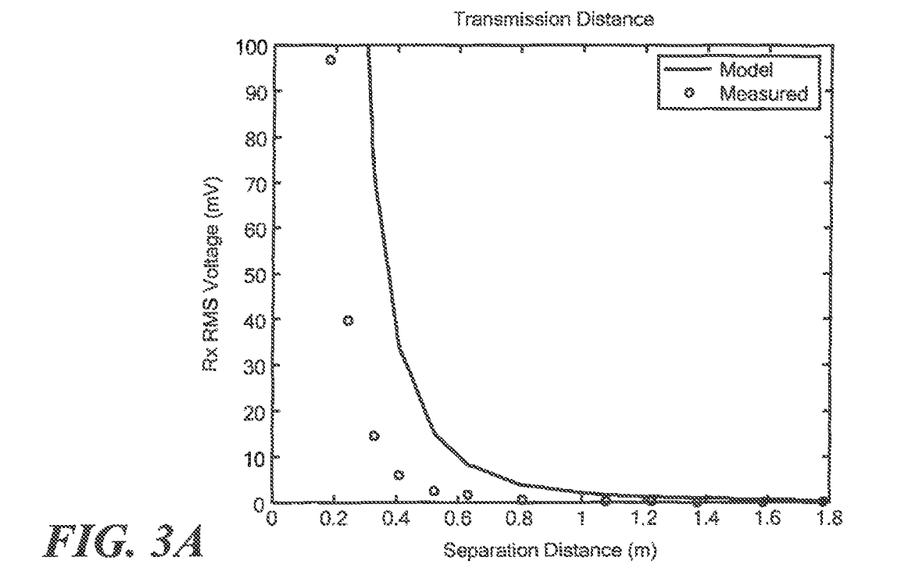
FIG. 3A is a graphical representation of transmission distance data and FIG. 3B is a graphical representation of dipole orientation effects.
Figure 3B:
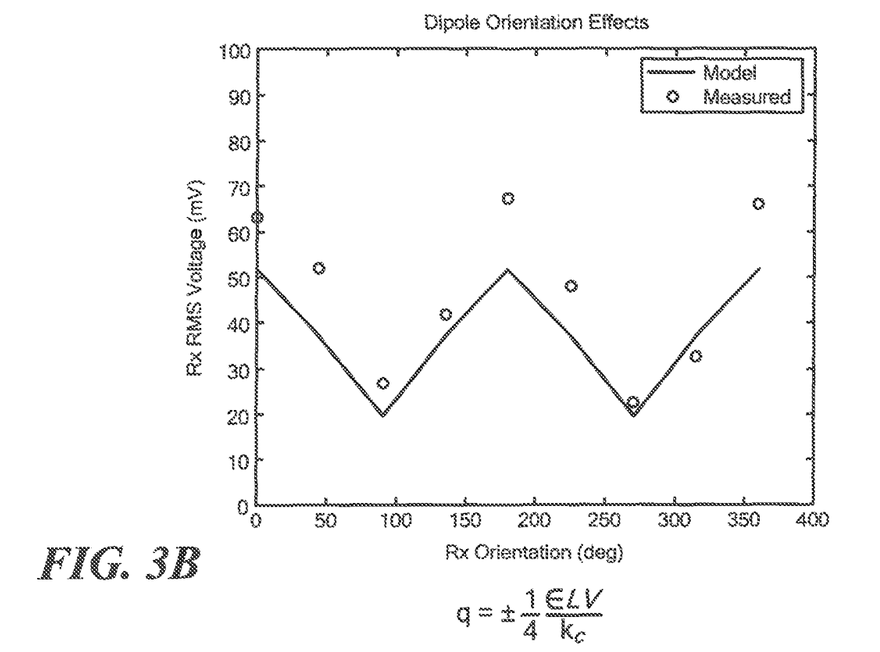

FIG. 3A shows signal transmission distance for separation distance versus receive RMS voltage for a model and measured signals and FIG. 3B shows dipole orientation effects in degrees versus receive RMS voltage.

Figure 4:
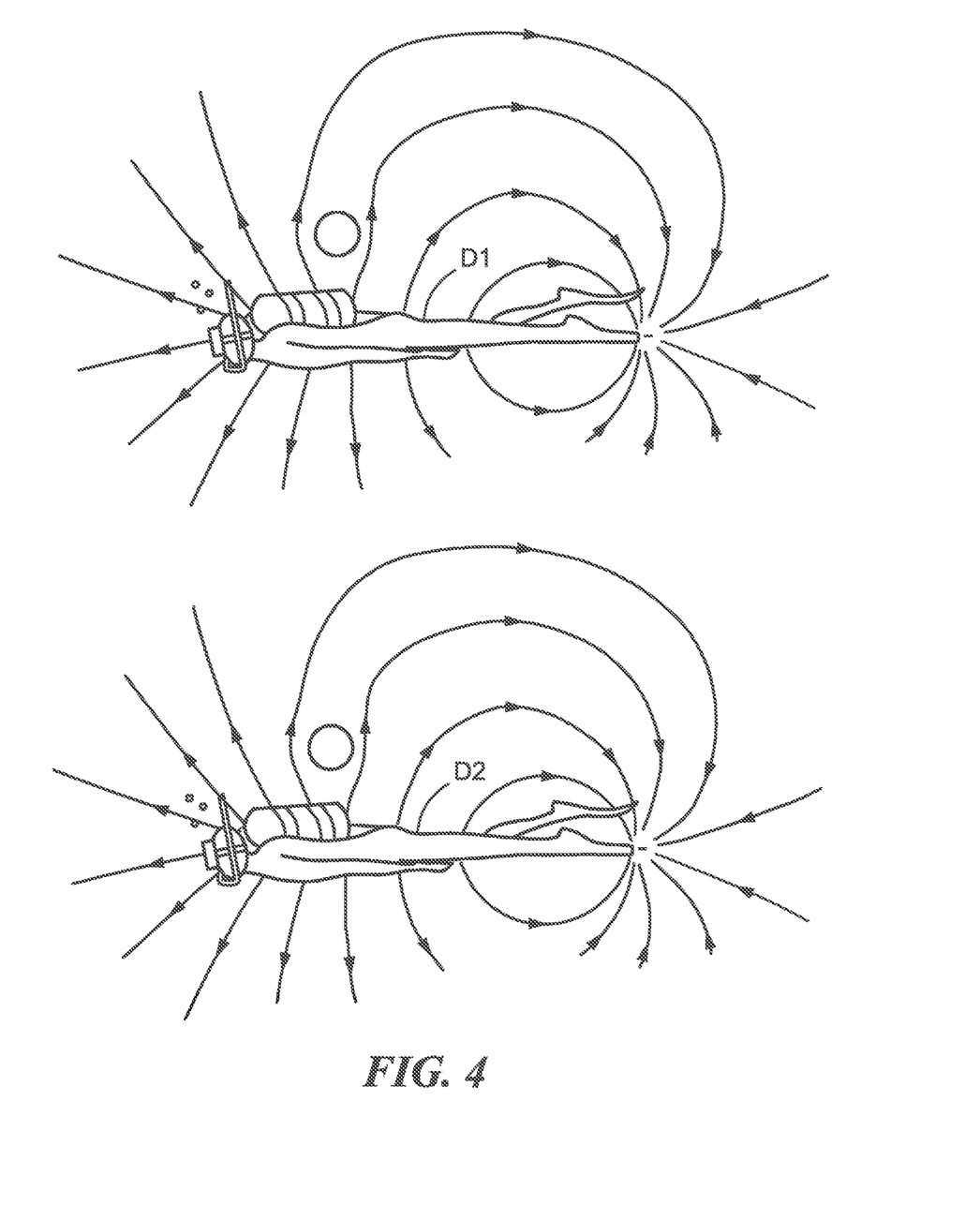
FIG. 4 is a schematic representation of signals generated by a near-field signal system that is part of a wetsuit.
Figure 5A:
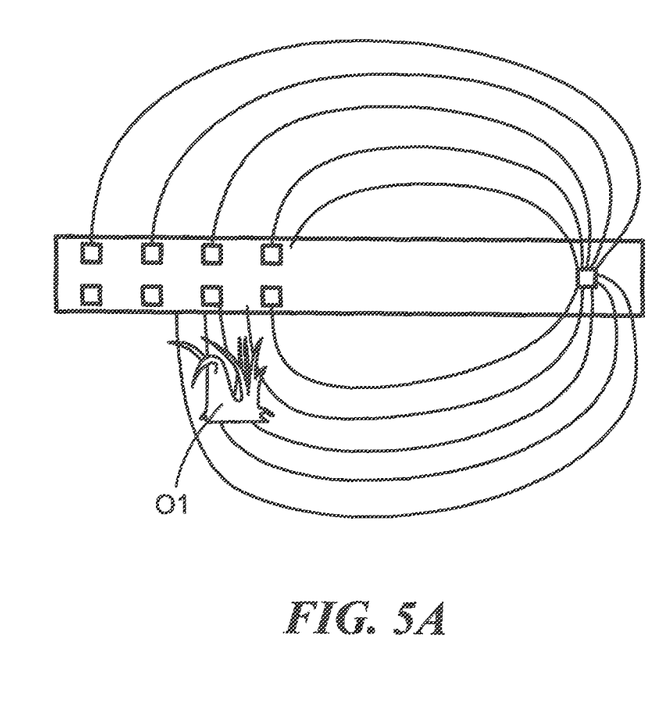
FIG. 5A shows an object not blocking field signals and FIG. 5B shows an object blocking field signals.
Figure 5B:
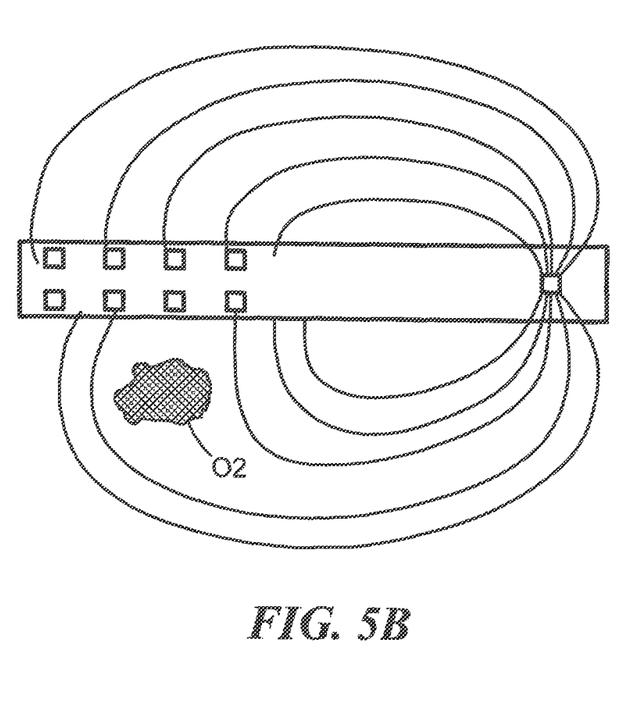

As shown in FIGS. 4 and 5A and 5B, the distance of an object can be determined using an 'electric image' projected on a sensor array for electrolocation wherein the ratio between maximal image slope and maximal image amplitude is the best predictor of distance. It will be appreciated that it may be challenging to accurately determine the distance of spherical objects. FIG. 4 shows wetsuits for respective divers D1, D2 having an integrated near-field signal system transmitting signals that are received by antenna arrays on other locations of the wetsuit. The divers D1, D2 can communicate with each other using their near field signal systems. Depending upon the complexity of the information to be sent, there may be a limit to how many signals may be sent simultaneously as interference can occur. Frequency separation can be used for multiple simple messages to be sent simultaneously, but as the bandwidth requirements increase with more complex information, at some point, the system may be limited to one send and one receive message to be sent within the range of the system. As the range of the system is roughly limited to less than 100 meters, operations outside of that range will not be affected and can operate freely.

FIG. 5A shows a scenario in which an object O1 that does not block the transmitted signal from being received by antenna arrays and FIG. 5B shows a scenario in which an object O2 blocks the transmitted signal. It is understood that the conductivity of the objects affect the 'electric image' detected by the antenna arrays. Active generation of an electric field enables perturbations to be detected. Objects less conductive than the water, such as rocks, create a 'dark spot' in the field. Objects more conductive than water create a 'bright spot' in the field.

As described above, sensors and electrodes embedded within a wetsuit produce electric fields which can be used for near-field navigation and/or communication. Information can be transmitted to users through heads-up display (HUD) and/or audio microphones and speakers.

Figure 6:
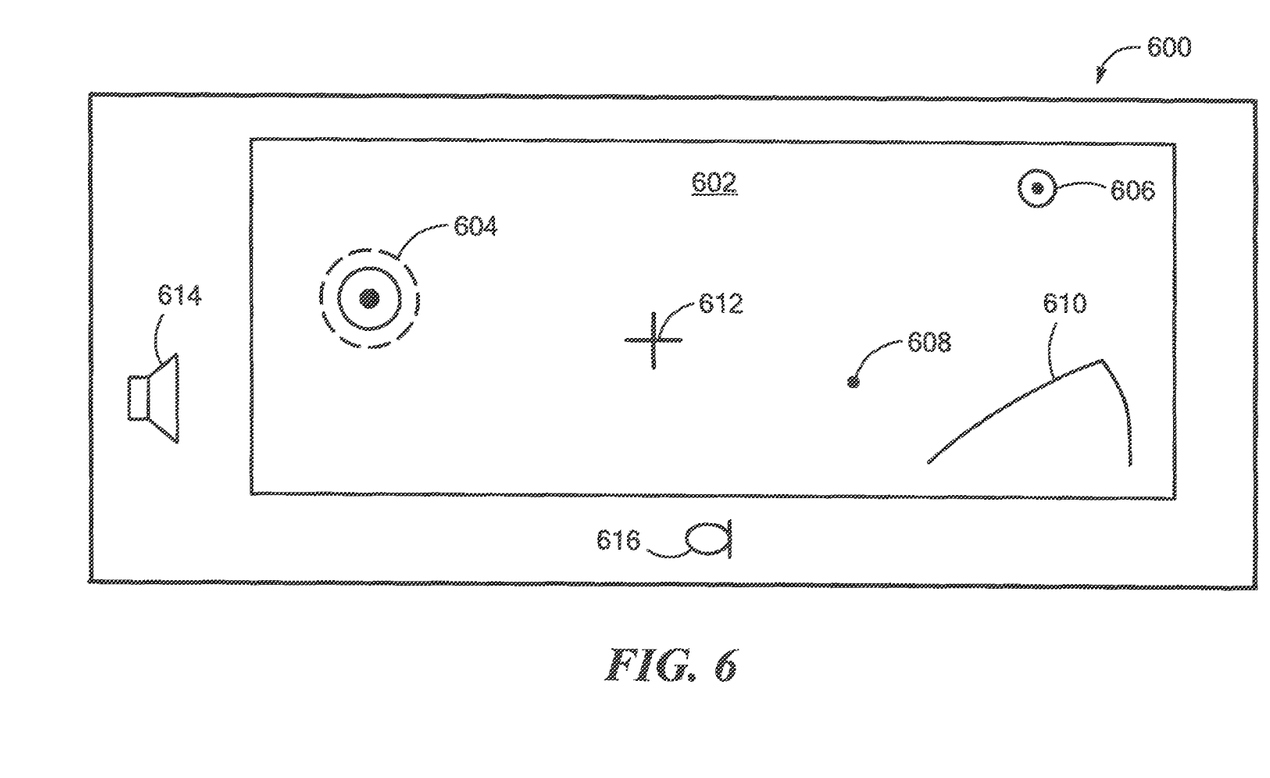
FIG. 6 is a schematic representation of a user interface including a heads up display and a sound system.

FIG. 6 shows an illustrative user interface 600 for a near-field signal system that can form part of a divers mask. In one example, the user interface 600 includes a heads up display (HUD) 602. In the illustrated embodiment, a first object 604 is shown that corresponds to a fellow diver in relatively close proximity that provides a strong signal. A second object 606 is likely to be a fellow diver that is farther from the user. A third object 608 is shown as a weak signal of unknown origin. A fourth object 610 is shown that generally corresponds to a geologic structure, such as a rock formation. The objects are shown in relation to a location 612 of the user.

In one embodiment, known divers transmit a signal that identifies each diver to the other divers. For example, the identify of divers on the HUD 602 can be included.

The mask can further include a loudspeaker 614 to generate sound for a user and a microphone 616 to receive speech from the user. It is understood that a variety of other information can be provided to the user from the display include LED indicators for various information. The display could be designed to, for example, display text messages, pictures, and/or video images.

Communication and navigation signals are identical in that they are emitted in the form of an electrical field but can be monitored differently. For communication, the signal is transmitted and received in the form of a frequency modulated waveform. In the case of the navigation or object detection function, the electrical field is monitored as a quasi static field. When a change is sensed in that field via signal processing, this information can be transmitted to the operator or vehicle. For example when a conductive object is placed within the field, the signal is amplified. Multiple receivers that have been monitoring the field can "see" the amplification and then transmit information about the conductivity, distance, bearing, and size of the object.

It is known that the conductivity of water ranges from about 200-2,000 uS/cm for fresh water and about 43-50 mS/cm for seawater depending upon the temperature and salinity. Salinity affects the conductivity of water by a factor of a thousand between fresh and seawater. In embodiments, the system is optimized based upon salinity/conductivity level. For example in high salinity water a high current/low voltage signal will be generated, whereas in fresh water, a high voltage/low amperage signal will be used.

Figure 7:
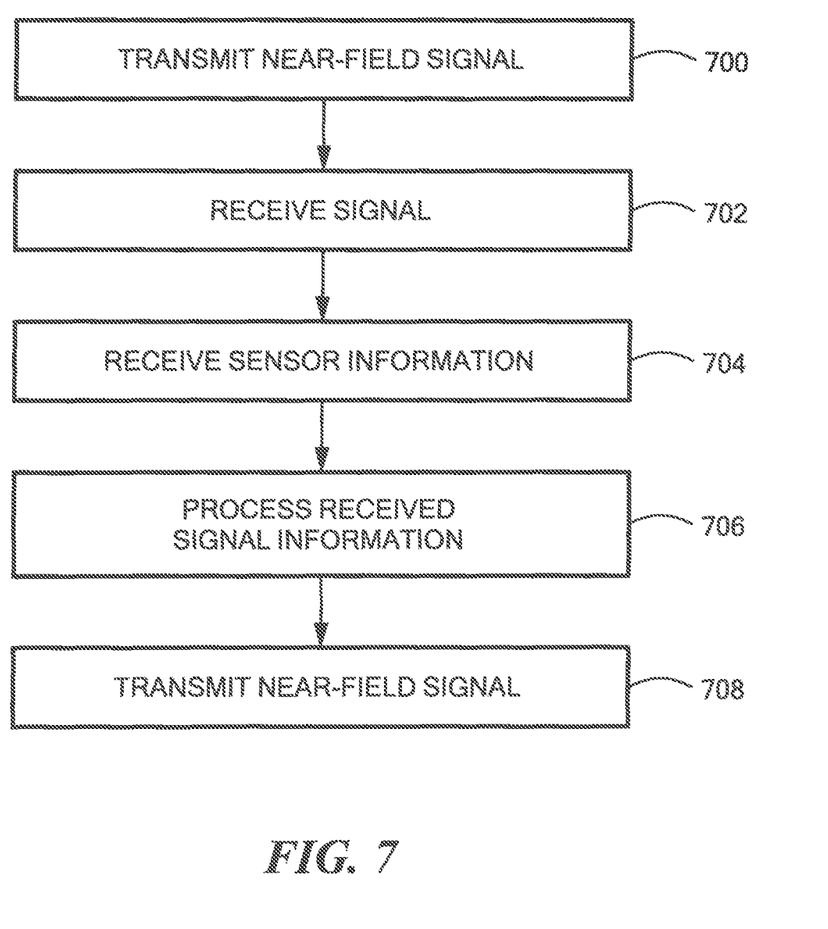
FIG. 7 is a flow diagram of an illustrative sequence of steps for near-field signal transmission and reception.

FIG. 7 shows an illustrative sequence of steps for providing near-field signal processing to provide communication and/or navigation underwater. In step 700, a near-field signal is transmitted by a first antenna underwater forming part of a near-field signal system. In one embodiment, the near-field signal system is integrated in a wetsuit. In step 702, a second antenna receives the signal transmitted by the first antenna. In step 704, sensor information is received from one or more sensors, such as salinity, temperature, depth, and the like. In step 706, the information received by the second antenna is processed to obtain communication information and/or navigation information. For example, a message from a fellow diver can be received or a rock formation can be detected. In step 708, information is transmitted by the first antenna for detection by a near-field system of a wetsuit for another diver. The transmitted information can include identification of the message sender.

It will be appreciated that a near-field signal system in accordance with embodiments of the invention are applicable to a wide variety of applications in which underwater signal transmission and reception are desirable. Embodiments can provide covert communication of voice and data, such as divers operating in an underwater environment. Other embodiments can provide covert navigation in zero visibility water, such as at night or very murky water. For example, divers would be able to 'see' in harsh environments, such as oil rigs, riverine works, and search and rescue. A search and rescue diver may be able to 'see' objects in low visibility situations using a near-field system embedded in a wetsuit. In addition, scuba divers can achieve covert communication, object detection, location of other divers, and/or location of electrically emitting objects. Underwater vehicles, such as UUVs can swarm groups of vehicles, detect objects in murky water, and effect covert communication with other UUVs. Manned craft can detect submarines covertly. Near-field systems can provide sub-sea network location and communication and covert inter sensor location and data relay. In other embodiments, near-field signals can manipulate fish, which respond to electrical fields.

Figure 8:
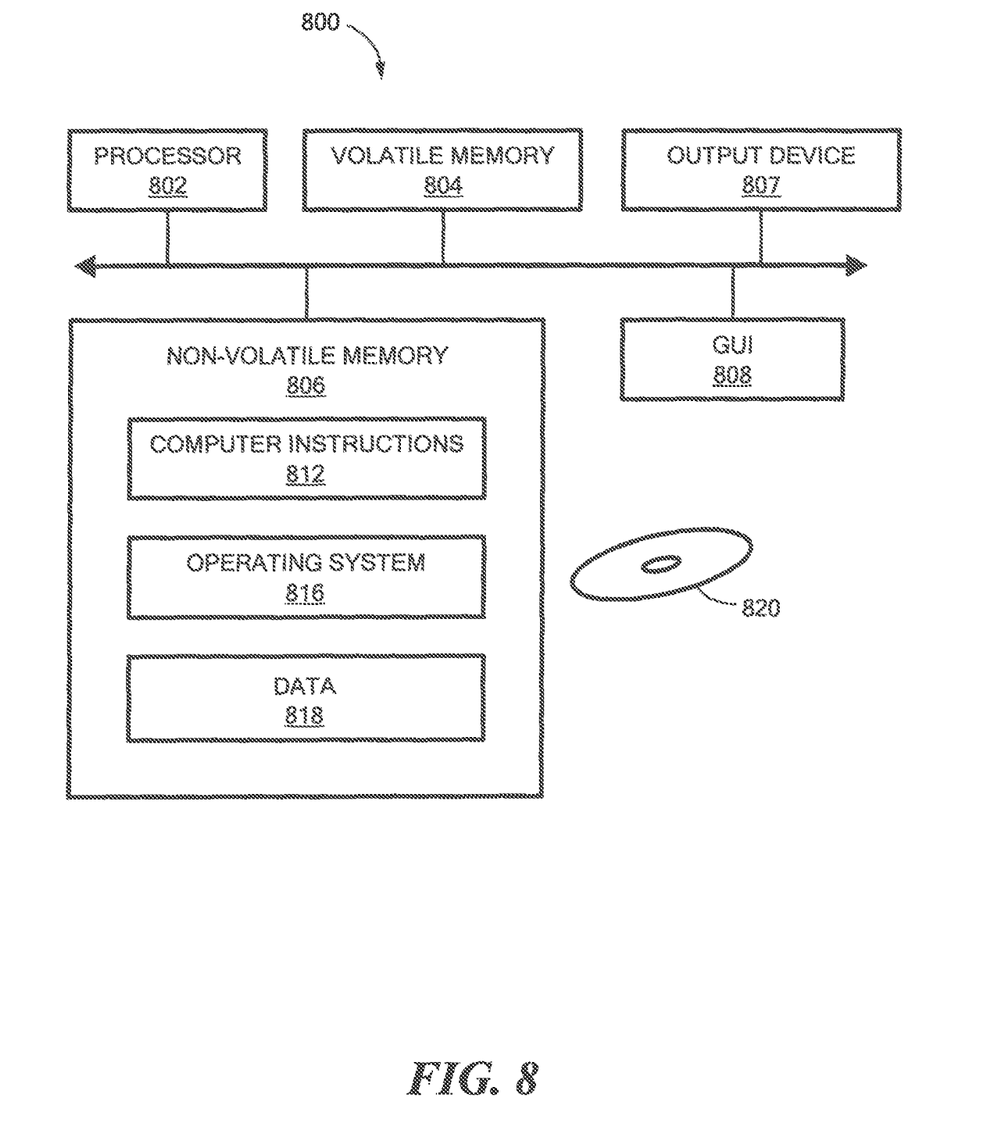
FIG. 8 is a schematic representation of an illustrative computer that can perform at least a portion of the processing described herein.

FIG. 8 shows an exemplary computer 800 that can perform at least part of the processing described herein. The computer 800 includes a processor 802, a volatile memory 804, a non-volatile memory 806 (e.g., hard disk), an output device 807 and a graphical user interface (GUI) 808 (e.g., a mouse, a keyboard, a display, for example). The non-volatile memory 806 stores computer instructions 812, an operating system 816 and data 818. In one example, the computer instructions 812 are executed by the processor 802 out of volatile memory 804. In one embodiment, an article 820 comprises non-transitory computer-readable instructions.

Processing may be implemented in hardware, software, or a combination of the two. Processing may be implemented in computer programs executed on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform processing and to generate output information.

The system can perform processing, at least in part, via a computer program product, (e.g., in a machine-readable storage device), for execution by, or to control the operation of, data processing apparatus (e.g., a programmable processor, a computer, or multiple computers). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer.

Processing may also be implemented as a machine-readable storage medium, configured with a computer program, where upon execution, instructions in the computer program cause the computer to operate.

Processing may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)).

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A near-field signal system to generate signals underwater, comprising:
    a signal processing module;
    a first antenna to transmit electrical near-field signals underwater coupled to the signal processing module;
    a second antenna to receive near-field signals underwater transmitted by the first antenna, wherein the second antenna is coupled to the signal processing module; and
    a salinity sensor to measure salinity of water coupled to the signal processing module, wherein a current and/or a voltage of the electrical near-field signals transmitted by the first antenna is adjusted based upon the measured water salinity.

2. The system according to claim 1, further including a temperature sensor to obtain temperature information for the water coupled to the control module.

3. The system according to claim 1, wherein the second antenna includes a dipole array.

4. The system according to claim 1, further including a user interface to display information on objects detected by the second antenna.

5. The system according to claim 4, wherein the user interface includes a head up display.

6. The system according to claim 1, wherein the user interface includes a sound generator.

7. The system according to claim 1, wherein the near-field signal system forms a part of a wetsuit.

8. The system according to claim 3, wherein the near-field signal system forms part of an underwater vehicle and the dipole array is located around the vehicle.

9. A method, comprising:
    measuring salinity of water using a salinity sensor,
    transmitting electrical near-field signals underwater by a first antenna, wherein a current and/or a voltage of the electrical near-field signals transmitted by the first antenna is based upon the measured water salinity;
    receiving near-field signals underwater transmitted by the first antenna; and
    processing the received near-field signals to provide information to a user.

10. The method according to claim 9, wherein the information comprises navigation information to avoid underwater objects.

11. The method according to claim 9, wherein the information comprises communication data from another underwater entity.

12. The method according to claim 9, further including using the measured water salinity to process the received near-field signals.

13. The method according to claim 9, further including using temperature information for the water coupled to process the received near-field signals.

14. The method according to claim 9, further including receiving the near-field signals with a second antenna that includes a dipole array.

15. The method according to claim 9, further including formatting the processed information for display to a user.

16. The method according to claim 9, wherein the first antenna forms a part of a wetsuit.

17. The method according to claim 9, wherein the first antenna forms a part of an underwater vehicle.

18. A system, comprising:
    a display;
    a signal processing means coupled to the display, the signal processing means to generate signals for transmission of electrical near-field signals underwater by a first antenna and to process near-field signals transmitted by the first antenna and received by a second antenna, and
    a salinity sensor to measure salinity of water coupled to the signal processing module, wherein a current and/or a voltage of the electrical near-field signals transmitted by the first antenna is adjusted based upon the measured water salinity.

19. A near field communication system for generating signals underwater, comprising:
    a signal processing module;
    a first antenna to transmit signals;
    a second antenna to receive near field signals originating from a further near field communication system that is underwater, wherein the first antenna and the second antenna are connected to the signal processing module, and
    a salinity sensor to measure salinity of water coupled to the signal processing module, wherein a current and/or a voltage of the signals transmitted by the first antenna is adjusted based upon the measured water salinity.

20. A near field signal system for generating signals underwater comprising:
    a signal processing module;
    a first antenna to transmit a navigation signal, a communication signal, or both;
    a second antenna to receive the navigation signal from the first antenna or a communication signal from a further near field signal system; and
    a salinity sensor to measure salinity of water coupled to the signal processing module, wherein a current and/or a voltage of the signal transmitted by the first antenna is adjusted based upon the measured water salinity;
    wherein first and second antennas are connected to the signal processing module, and wherein the signal processing module is configured to interpret the received signals as either the navigation signal from the first antenna or the communication signal from the further near field signal system.

21. The method according to claim 9, wherein the information comprises multiple messages, and frequency separation is used for sending the multiple messages to the user substantially simultaneously.

22. The method according to claim 9, wherein the information comprises locations of conductive and non-conductive objects.

* * * * *